United States Patent [19]

Canfield et al.

[11] Patent Number: 4,851,356
[45] Date of Patent: Jul. 25, 1989

[54] IMMUNOASSAY FOR HUMAN CHORIONIC GONADOTROPIN

[75] Inventors: Robert E. Canfield, New York; Elmo G. Armstrong, Bronx; Paul H. Ehrlich, New York, all of N.Y.; Steven Birken, Dumont, N.J.

[73] Assignee: The Trustees of Columbia University in the City of New York, New York, N.Y.

[21] Appl. No.: 72,802

[22] Filed: Jul. 14, 1987

Related U.S. Application Data

[63] Continuation of Ser. No. 767,158, Aug. 19, 1985, abandoned, which is a continuation of Ser. No. 492,210, May 6, 1983, abandoned.

[51] Int. Cl.⁴ .................. G01N 33/76; G01N 33/535; G01N 33/543
[52] U.S. Cl. ..................................... 436/510; 436/518; 436/529; 436/548; 436/804; 436/813; 436/814; 436/818; 436/823; 935/110; 435/7; 435/68; 435/172.2; 435/240.27; 435/188; 435/192
[58] Field of Search ............. 435/7, 28, 68, 70, 172.2, 435/188, 192, 240.27; 436/510, 518, 529, 536, 542, 547, 548, 540, 804, 813, 814, 818, 823; 935/110

[56] References Cited

U.S. PATENT DOCUMENTS 4,376,110  3/1983  David et al. ..................... 436/513
4,514,505  4/1985  Canfield et al. ................. 436/500

OTHER PUBLICATIONS

Shimuzu, S. Y. et al. (Clin. Chem., vol. 28, No. 3, pp. 546-547, 3-1982).
Moyle et al. (Proc. Ntl. Acad. Sci. USA, vol. 79, pp. 2245-2249, 4-1982).
Wehmann et al. (Clin. Chem, vol. 27, No. 12, pp. 1997-2001, 12-1981).
Wehmann, R. F. et al. (Am. J. Obstet. Gynecol., vol. 140, pp. 753-757, 8-1981).
Vaitukaitis, J. L. et al, Amer. J. Obstet, Gynecol., vol. 113, pp. 751-758 (7-15-1972).
Birken, S. et al, Endoerinology, vol. 110, No. 5, pp. 1555-1563 (5-1982).
Birken, S., Reprod. Processes Contracept., Chapter 24, pp. 529-534 (1981), McKerns, K. W. ed, Plenum Press, N.Y., N.Y.

*Primary Examiner*—Margaret Moskowitz
*Attorney, Agent, or Firm*—John P. White

[57] ABSTRACT

An immunoassay for detecting and measuring hCG in a sample includes an antibody directed to the carboxy terminal portion of the β subunit of hCG and a monoclonal antibody directed to a determinant on hCG at a locus sufficiently remote from the carboxy terminal portion of the β subunit of hCG that both antibodies can simultaneously bind to hCG, wherein at least one of the antibodies is delectable when both are bound to hCG.

In a presently preferred embodiment, an immunoassay for hCG or hCBβ in urine includes a purified, labeled or detectable serum-derived antibody directed to the carboxy-terminal portion of the β subunit of hCG and a matrix-bound monoclonal antibody directed to a locus on the β subunit sufficiently remote from the carboxy-terminal portion that both antibodies can simultaneously bind to hCG or hCGβ.

19 Claims, 2 Drawing Sheets

IMMUNOASSAY FOR HUMAN CHORIONIC GONADOTROPIN

The invention described herein was made in the course of work under grant numbers HD-15454 and RR-00645 from the National Institutes of Health, United States Department of Health and Human Services, U.S.A.

This application is a continuation of U.S. Ser. No. 767,158, filed Aug. 19, 1985, abandoned, which is a continuation of U.S. Ser. No. 492,210, filed May 6, 1983, now abandoned.

BACKGROUND OF THE INVENTION

Throughout this application various publications are referred to to provide background information useful for a complete understanding of the invention. The disclosures of these references are hereby incorporated in their entireties into the present application.

Immunoassays for human chorionic gonadotropin (hCG) are known and have been widely used, particularly in the diagnosis of pregnancy. Recent advances in immunology involving hybridomas and monoclonal antibodies have greatly increased the sensitivity of previous immunoassays. See, for example, Ehrlich, P.H. et al., Journal of Immunology 128:2709 (1982); Wada, H.G. et al., Clin. Chem., 28:1862 (1982); Shimizu, S.Y. et al., Clin. Chem., 28:546 (1982); and Pettersson, K. et al., Clin. Chem., 29:60 (1983). Serum-derived antibodies have also been employed. See, for example, Sekiya, T. et al., Acta Endocrinologica 97:562 (1981); Ayala, A.R. et al., J. Clinical Endocrinology and Medicine, 47:767 (1978) and Wehmann, R.E. et al., Amer. J. of Obstetrics and Gynecology, 140:753 (1981). Immunoassays involving serum-derived antibodies have included antibodies directed to the unique carboxy terminal portion of the $\beta$ subunit of hCG (ibid.; and Birken, S. et al., Endocrinology, 110:1555 [1982]).

Although previous improvements in hCG immunoassays have provided increased sensitivity or specificity, or both, it has not been possible until the present invention to obtain the greatly enhanced sensitivity and almost absolute specificity achieved using the immunoassay disclosed and claimed herein. This new immunoassay permits detection of smaller increases in hCG levels, and detection much sooner after insemination, than previously possible. It also permits hCG measurements in cancer diagnosis unimpaired by significant hLH cross-reactions.

SUMMARY OF THE INVENTION

This invention concerns an immunoassay for detecting hCG or measuring the level of hCG in a sample. The assay includes an antibody directed to the carboxy terminal portion of the $\beta$ subunit of hCG and a monoclonal antibody directed to a determinant on hCG at a locus sufficiently remote from the carboxy terminal portion of the $\beta$ subunit of hCG that both antibodies can simultaneously bind to hCG, wherein at least one of the antibodies is detectable when both are bound to hCG. In a presently preferred embodiment the immunoassay can detect or measure levels of hCG or hCG$\beta$ in a urine sample and includes a detectable, purified, serum-derived antibody directed to the carboxy terminal portion of the $\beta$ subunit of hCG and a matrix-bound monoclonal antibody directed to a locus on the $\beta$ subunit sufficiently remote from the carboxy terminal portion that both antibodies can simultaneously bind to hCG. The assay may be used to detect hCG or to measure hCG levels in urine samples. In this way the presence of hCG-producing neoplasms, subclinical spontaneous abortions and ectopic pregnancies can be diagnosed.

DETAILED DESCRIPTION OF THE INVENTION

Figure 1:
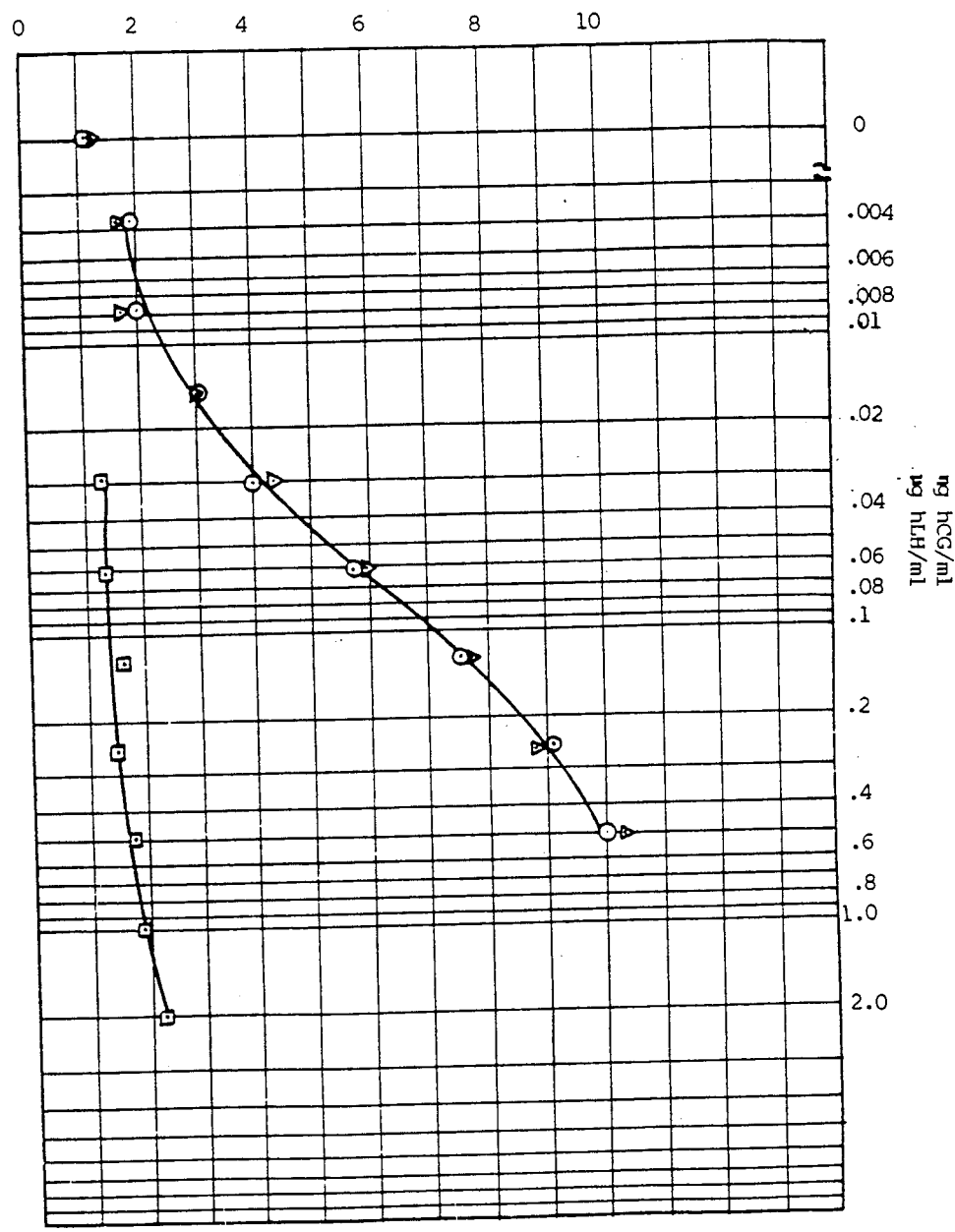
FIG. 1 is a standard curve showing use of the assay to measure hCG in buffer (⊙---⊙) and in urine (▲---▲) and to show extent of cross-reactivity with hLH in urine (□---□).

Recent improvements in immunoassay technologies, particularly the development of monoclonal antibodies, have permitted improvements in the sensitivity of assays for human chorionic gonadotropin (hCG). However, until the present invention assays have not been available which permit detection of increases in hCG levels a few days after insemination and which possess essentially absolute specificity for hCG, having no cross-reactivity with hLH.

Specifically, this invention provides an immunoassay for detecting hCG or measuring levels of hCG, or both, in a sample. The immunoassay includes an antibody directed to the carboxy terminal portion of the $\beta$ subunit of hCG which is a unique peptide sequence not found in hLH. The immunoassay also includes a monoclonal antibody directed to a determinant on hCG at a locus sufficiently remote from the carboxy terminal portion of the $\beta$ subunit that both antibodies can simultaneously bind to hCG. Finally, at least one of the antibodies is capable of detection when both antibodies are bound to hCG.

Although in principle any antibody directed to the carboxy terminal portion of the $\beta$ subunit of hCG would be effective, the presently available and preferred antibodies are purified, serum-derived antibodies. Examples include R525 and R529 as described more fully hereinafter. However, the present invention is not limited to serum-derived antibodies and also encompasses monoclonal antibodies directed to the carboxy terminal portion of the $\beta$ subunit if and when efforts to produce such monoclonal antibodies are successful.

Either antibody or both antibodies are capable of detection when the antibodies are bound to hCG. Various means for rendering an antibody detectable are known to those skilled in the art. Merely by way of example, suitable means include radioactive labeling, e.g., $^{125}I$ labeling, fluorescent labeling or linkage to an enzyme which catalyzes a detectable reaction, that is, an ELISA approach, e.g., linkage of an antibody to horseradish peroxidase. An additional approach involves the use of a third antibody directed to one of the antibodies of the assay where the third antibody, either serum-derived or monoclonal, is detectable, e.g., labeled with a radioactive isotope or a fluorescent moiety.

The immunoassay of the present invention may be carried out totally in liquid phase, totally in solid phase or in a mixed liquid/solid system. Presently it is preferred that one of the antibodies, preferably the monoclonal antibody directed to a locus remote from the carboxy terminal portion of the β subunit be attached to a solid matrix, e.g., agarose or Sepharose.

Although the immunoassay may be used with either urine, plasma, serum or other samples, it is particularly desirable to employ the immunoassay on urine samples because of the greater ease and convenience of obtaining such samples. This is, in fact, one of the substantial advantages provided by the present invention since most presently available immunoassays for hCG are not suitable for use with urine samples.

The presently preferred embodiment of the invention involves an immunoassay for detecting hCGβ or measuring levels of hCGβ, and hereby detecting or measuring hCG. This immunoassay includes a purified, serum-derived antibody directed to the carboxy terminal portion of the β subunit of hCG and a monoclonal antibody directed to a locus on the β subunit sufficiently remote from the carboxy terminal portion that both antibodies can simultaneously bind to hCG. In the preferred embodiment the purified, serum-derived antibody is detectable when both antibodies are bound to hCGβ, alone or as hCG, and the monoclonal antibody is attached to a solid matrix.

This invention also concerns a purified antibody to the carboxy terminal portion of the β subunit of hCG, preferably labeled or otherwise detectable, e.g., $^{125}$I-labeled.

The immunoassay of this invention provides a method of detecting hCG or measuring the level of hCG, or both, in a urine sample. The sample to be tested is placed in the immunoassay under suitable conditions permitting formation of a detectable or measurable complex with hCG. The resulting complex may then be detected if present or the level of hCG present determined by reference to a standard containing a known amount of hCG.

Measurements of hCG levels in turn can be used in the diagnosis or identification of disorders which involve production, or elevated levels, of hCG. Examples of such disorders include certain neoplasms, e.g., male testicular cancer, subclinical spontaneous abortions and ectopic pregnancies.

Methods for utilizing immunoassays for such purposes are well known to those skilled in the art and therefore are not described hereinafter in greater detail.

The following section entitled "EXPERIMENTAL DETAILS" is set forth to aid in an understanding of the present invention but is not intended, and should not be construed, to limit the invention as defined by the claims which follow thereafter.

EXPERIMENTAL DETAILS

Materials and Methods

Reagents

The antibodies used in this experiment were R525 and R529, Birken, S. et al., Endocrinology, 110:1555 (1982), rabbit antisera directed against the hCGβ- CTP determinants, and B101, Ehrlich, P. H. et al., Journal of Immunology, 128:2709 (1982), a mouse monoclonal antibody directed against an hCGβ conformational determinant. The methods of preparation and characteristics of these antibodies were as published in the preceding two cited references.

The preparation of highly purified hCG and hCGβ subunit have been previously described. Canfield, R. E. and Morgan, F. J., in: *Methods in Investigative and Diagnostic Endocrinology*, edited by Berson, S. A. and Yalow, R. S., North-Holland, Amsterdam, p727 (1974). Human luteinizing hormone was a gift from the National Pituitary Agency (University of Maryland School of Medicine) NIAMDD, NIH. Concanavalin A covalently linked to agarose (Con A Sepharose), anhydrous α-methyl-D-mannoside and bovine γ-globulin, Cohn fraction II were purchased from Sigma Co. Cyanogen bromide (CnBr) activated Sepharose 4B was obtained from Pharmacia Fine Chemicals and DEAE Affi-Gel Blue from Bio-Rad Laboratories. The preceding purchased materials were used in accordance with the manufacturers' instructions.

Monoclonal Antibody Production in Ascites Fluid, Purification and Coupling to Sepharose 4B The production of monoclonal anti-hCGβ was amplified utilizing the mouse ascites tumor system. Zola, H. and Brooks, D. in: *Monoclonal Hybridoma Antibodies: Techniques and Applications*, edited by J. G. R. Hurrell, CRC Press, Inc., Boca Raton, Fla., p50 (1982). One million B101 producing hybridoma cells were injected into each of thirty CD2F1 strain mice (West Seneca Laboratories) two weeks after they had been primed with one-half ml of pristane. Collection of ascites fluid commenced three weeks after injection of the cells and continued for two months. A total of 330 ml of ascites fluid was pooled and stored at −80° C.

One aliquot of forty-six mls was dialysed extensively against 0.025 M Tris-HCl, pH 7.5, containing 0.05 M NaCl and 0.02% sodium azide at 4° C. The dialysate was applied to a 25×300 mm column of DEAE Affi-Gel Blue and eluted in five ml fractions with the same buffer used for dialysis. One hundred fractions containing the peak absorbance of 280 nm were pooled. The total amount of protein recovered in the preparation was calculated to be 1.46 g using the method of Warburg and Christian. Warburg, O. and Christian, W., Biochem. Z., 310:384 (1941). Electrophoresis of the preparation on nonreducing SDS polyacrylamide gels, Weber, K. and Osborn, M., J. Biol. Chem., 244:4406 (1969), indicated that at least 80% of the protein content was γ-globulin.

Forty mls of the partially purified ascites preparation containing approximately 80 mg γ-globulin was dialysed against 0.1 M NaHCO$_3$, pH 8.0, containing 0.5 M NaCl at 4° C. The dialysate was then coupled to ten grams of CnBr activated Sepharose 4B according to the manufacturer's instructions. A 50% suspension (vol.-/vol.) of B101 coupled Sepharose 4B was prepared in 10 mM phosphate buffered saline, pH 7.4, containing 10 mM Na2EDTA, 0.1% sodium azide and 0.1% bovine γ-globulin (buffer B) and stored at 4° C.

Purification of Rabbit Anti hCGβ-CTP (R525) and Iodination

Ten mgs of hCGβ was coupled to two grams of CnBr activated Sepharose 4B. The hCGβ coupled Sepharose 4B was used to form an 0.9×10 cm column which was used for affinity purification of R525. A 54 ml pool of R525 from several different bleeds between boostings was recycled over the column continuously for 30 hours at 4° C using a peristaltic pump. The column was washed extensively with saline to remove loosely adhering material. The column was then eluted successively with 20 ml of 3M guanidine-HCl, pH 3.0, and 20 ml of 6 M guanidine-HCl, pH 3.0. The effluent was collected in one ml fractions and the absorbance at 280 nm determined. The absorbance profile had two discrete protein peaks corresponding in position to the areas of elution with 3 M and 6 M guanidine-HCl. The fractions having the peak absorbance at 280 nm were pooled and then dialysed extensively against 10 mM sodium acetate, pH 5.5, followed by 0.3 M NaPO$_4$, pH 7.5, at 4° C. The dialysed preparations, an aliquot of the unpurified R525 pool and also the R525 pool which had been circulated over the hCGβ affinity column were tested for their ability to bind $^{125}$I-hCG. Only the unpurified R525 pool and the purification product eluted from the column with 6 M guanidine-HCl had significant binding. A 1:1,500 dilution from a total volume of 5.7 ml of the purified R525 bound 50% of the trace as opposed to a 1:600 dilution of the unpurified antiserum pool. The total protein content of the purified R525 was calculated to be 1.9 mg. Warburg, O. and Christian, W, Biochem Z., 310:384 (1941).

Thirty μg of the purified R525 was radiolabeled with lmCiNa $^{125}$I (Amersham) using Iodogen (Pierce Chemical Company) as the oxidizing agent. Fraker, P. J. and Speck, Jr., J. D., Biochem. Biophys. Research Comm., 80:849 (1978). The specific activity of the iodinated product was approximately 20 μCi/μg protein.

Conduct of Sandwich Assay

The conditions for the sandwich assay described below are the result of optimization by detailed analysis of reagent concentrations, incubation times and temperatures required to give maximum hCG binding. Prior to assay, urine samples were adjusted to pH 7.4 with NaOH and centrifuged at 3000×g for 15 minutes Duplicate or triplicate four ml aliquots of urine, standards containing 0.004–0.5 mg hCG/ml in Buffer B, or Buffer B alone (for determination of nonspecific bindings; binding of trace [$^{125}$I-R525] in the absence of hCG) were pipetted into 12×75 mm polystyrene tubes. Two-tenths ml of a 6.25% suspension of B101 coupled Sepharose 4B in Buffer B, containing approximately 25μg γ-globulin, was pipetted into each tube. The tubes were capped, placed horizontally on a Labquake Shaker (Labindustries) and incubated for two hours at room temperature with shaking in order to extract hCG from the samples. The tubes were centrifuged for 15 minutes at 3,000×g. The supernatants were removed by aspiration, and the B101-Sepharose 4B pellets washed 2× with 2 ml Buffer B+1% Tween 20.

One-tenth ml of Buffer B containing 50,000 CPM $^{125}$I-R525 was added to each tube. The samples were incubated vertically for 48–72 hours at 4° C. with shaking on the Labquake Shaker. The tubes were then washed three times with 2 ml of Buffer B +1% Tween 20 to reduce nonspecific binding. The radioactivity remaining after washing was determined in a Packard Auto-Gamma Scintillation Spectrometer. Data reduction for the generation of standard curves was accomplished using a four parameter logistic fit. Rodbard, D. and Hutt, D. M., *Proceedings Symposium on Radioimmunoassay and Related Procedures in Medicine,* International Atomic Energy Agency, Vienna, Austria, Unipub, New York, p165 (1974).

Conduct of the hCG RIA

The hCG radioimmunoassay was conducted using the R529 antiserum to the hCG8 CTP determinants to measure hCG extracted from urine with concanavalin A as described by Wehmann, et al. Wehmann, R. E., et al., Clinical Chemistry, 27:1997 (1981).

Patients

First morning voided and random urines collected by normal volunteers at the Columbia Presbyterian Medical Center were used in order to establish the normal range of hCG excretion. The measurement of hCG for detection of early pregnancy was conducted using first morning voids provided by patients in the Department of Obstetrics and Gynecology, Columbia College of Physicians and Surgeons. These were normal women who were artificially inseminated because of the male partners' infertility.

In order to correct for difference in the specific gravities of the various urines collected, urinary hCG concentration was normalized to creatinine concentration.

Results

Sandwich Assay Standard Curve

A typical standard curve generated for hCG binding in the sandwich assay is shown in FIG. 1. The hCG dosages which give binding equivalent to 10% and 90% of Bmax (ED$_{10}$ and ED$_{90}$) have been tentatively accepted as the limits of the usable range of the standard curve. In the assay demonstrated ED$_{10}$ and ED$_{90}$ correspond to 0.01 and 0.50 ng hCG/ml, giving a fiftyfold usable range. The Nonspecific Binding (NSB) in the assay is reduced to an acceptable level by extensive washing of the pellet with buffer containing Tween 20 and bovine γ-globulin. In the assay represented NSB was 2.5% of the total counts added.

FIG. 1 also shows the dose response curve of hCG extracted from normal male urine which had been spiked with dosages identical to those used in the standards. The dose response curve for hCG in urine is essentially identical to that for hCG in Buffer B. The slope and ED$_{50}$ of the dose response curve were 1.173 and 0.066 ng/ml for hCG in urine, compared to 1.098 and 0.072 ng/ml for hCG in buffer.

The dose response curve for hLH added to normal male urine is also shown in FIG. 1. It should be noted that the units for hLH concentration are μg/ml as opposed to ng/ml for hCG concentration. A concentration of 2 μg hLH/ml is required to obtain a dose response equivalent to 0.01 ng hCG/ml. Thus, the cross-reactivity of this concentration of hLH in the sandwich assay is 0.0005% on the basis of mass. This level of hLH is approximately fifty fold higher than those present in urine from women at the mid-cycle hLH surge. Saxena, B. B. et al., Fertility and Sterility, 28:163 (1977). Therefore, physiologic concentrations of hLH are incapable of interfering in the sandwich assay.

In summary, FIG. 1 shows that the assay is equally effective for the measurement of hCG in buffer and in urine, highly sensitive, i.e., capable of detecting hCG at levels down to 0.004 ng/ml and that cross-reactivity with hLH is exceptionally low, i.e., about 0.0005%, thereby rendering the assay absolutely specific for hCG.

Figure 2:
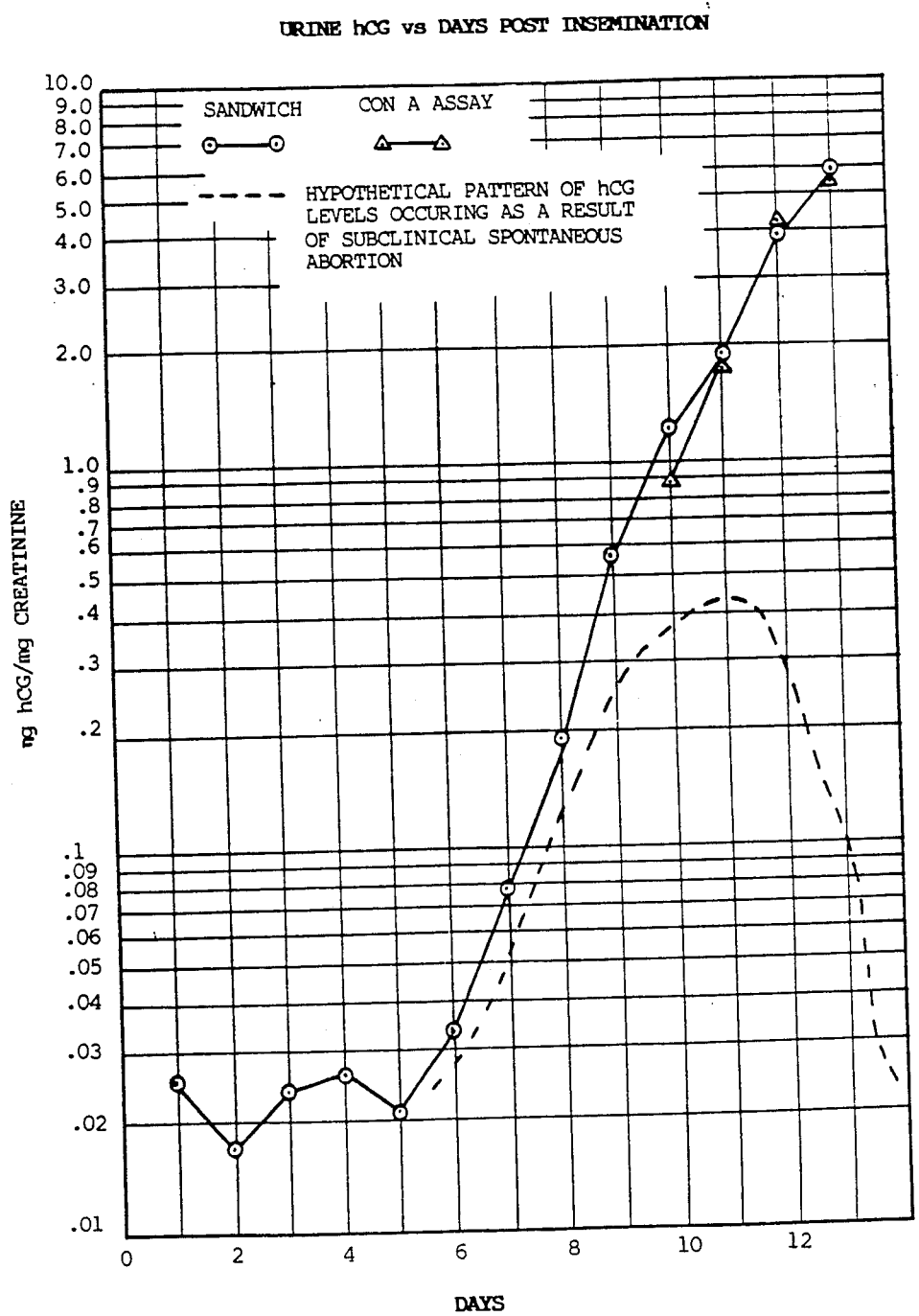
FIG. 2 illustrates the sensitivity of a conventional radioimmunoassay (Con A Assay, ▲---▲) as compared with the newly developed sandwich assay, (⊙---⊙) in the measurement of hCG levels in an artificially inseminated female patient. Also depicted is the hypothetical pattern of hCG levels occurring as a result of subclinical spontaneous abortion (----).

FIG. 2 shows the use of the assay to measure hCG levels in the urine of an artificially inseminated female patient at various days after insemination. By way of comparison FIG. 2 also shows the use of a standard radioimmunoassay to measure hCG levels in the same patient's urine. As is clearly indicated in FIG. 2, the assay of the present invention is capable of detecting elevated hCG levels after the sixth day following insemination. By contrast, the standard RIA (sandwich assay) is less sensitive and cannot detect hCG until the tenth day following insemination.

FIG. 2 also illustrates the application of the assay in the diagnosis of subclinical spontaneous abortion. The hypothetical pattern illustrated in FIG. 2 shows that the standard RIA is incapable of detecting either the rise or the fall of hCG as the result of subclinical spontaneous abortion while the assay of the present invention will be able to do so because of its much greater sensitivity.

What is claim is:

1. A two-site immunoassay for detecting and measuring an increase in the concentration of hCG in a urine sample from a pregnant woman less than ten days after insemination, wherein the immunoassay is capable of detecting hCG at levels down to about 0.004 ng/ml and exhibits cross reactivity with hLH of about 0.0005%, which comprises obtaining the urine sample from the pregnant woman, adjusting the pH of the urine sample to pH 7.4, contacting the resulting urine sample with both an antibody directed specifically to the carboxyl terminal portion of the $\beta$ subunit of hCG and a monoclonal antibody directed to a determinant on hCG at a locus sufficiently remote from the carboxy terminal portion of the subunit of hCG that both antibodies can be simultaneously bound to hCG, wherein one of the antibodies is attached to a solid matrix and wherein at least one of the antibodies is detectable when both antibodies are bound to hCG, so as to form a detectable and measurable complex which includes the antibodies and hCG, then detecting and measuring the resulting complex, and thereby detecting and measuring the increase in the concentration of hCG in the urine sample.

2. An immunoassay according to claim 1, wherein the antibody directed to the carboxy terminal portion of the $\beta$ subunit of hCG is a essentially purified, serum-derived antibody.

3. An immunoassay according to claim 1, wherein the antibody directed to the carboxy terminal portion of the $\beta$ subunit of hCG is a monoclonal antibody.

4. An immunoassay according to claim 1, wherein the antibody directed to the carboxy terminal portion of the $\beta$ subunit of hCG is detectable.

5. An immunoassay according to claim 4, wherein the detectable antibody is radioactively labeled.

6. An immunoassay according to claim 5, wherein the antibody is labeled with $^{125}I$.

7. An immunoassay according to claim 4, wherein the antibody is linked to an enzyme which catalyzes a detectable reaction.

8. An immunoassay according to claim 7, wherein the enzyme is horseradish peroxidase.

9. An immunoassay according to claim 4, wherein the antibody is detectable upon formation of a complex with a third antibody which is labeled.

10. An immunoassay according to claim 2, wherein the antibody is R 525 or R 529.

11. An immunoassay according to claim 10, wherein the R 525 pr R 529 rabbit polyclonal antibody is labeled with $^{125}I$.

12. An immunoassay according to claim 1, wherein the antibody directed to the carboxy terminal portion of the $\beta$ subunit of hCG is attached to a solid matrix.

13. An immunoassay for hCG$\beta$ according to claim 1, wherein the monoclonal antibody is directed to a determinant on the $\beta$ subunit of hCG.

14. An immunoassay according to claim 13, wherein the monoclonal antibody is B101 mouse monoclonal antibody.

15. An immunoassay according to claim 1, wherein the monoclonal antibody directed to a remote determinant on hCG is detectable.

16. An immunoassay according to claim 1, wherein the monoclonal antibody directed to a remote determinant on hCG is attached to a solid matrix.

17. An immunoassay according to claim 16, wherein the matrix is agarose or Sepharose.

18. A method of diagnosing for the presence of neoplasms producing hCG such as those associated with testicular cancer comprising measuring hCG levels according to the method of claim 1 and comparing the measured level with levels of hCG associated with neoplasms.

19. A two-site immunoassay for detecting and measuring an increase in the concentration of hCG or hCG$\beta$ in urine sample from a pregnant woman less than ten days after insemination, wherein the immunoassay is capable of detecting hCG at levels down to about 0.004 ng/ml and exhibits cross-reactivity with hLH of about 0.0005%, which comprises obtaining the urine sample from the pregnant woman, adjusting the pH of the urine sample to pH 7.4, contacting the resulting urine sample with both an essentially to the carboxyl terminal portion of the $\beta$ subunit of hCG and a monoclonal antibody directed to a determinant on hCG or hCG$\beta$ at a focus on the $\beta$ subunit of hCG sufficiently remote from the carboxyl terminal portion of the $\beta$ subunit that both antibodies can be simultaneously bound to hCG, wherein the essentially purified, serum-derived antibody is detectable when both antibodies are bound to hCG or hCG$\beta$ and wherein the monoclonal antibody is attached to a solid matrix, so as to form a detectable and measurable complex which includes the antibodies and hCG or hCG$\beta$, then detecting and measuring the resulting complex, and thereby detecting and measuring the increase in the concentration of hCG in the urine sample.

* * * * *

UNITED STATES PATENT AND TRADEMARK OFFICE
CERTIFICATE OF CORRECTION

PATENT NO. : 4,851,356

DATED : July 25, 1989

INVENTOR(S) : Robert E. Canfield, Elmo G. Armstrong, Paul H. Ehrlich and Steven Birken It is certified that error appears in the above-identified patent and that said Letters Patent is hereby corrected as shown below: ON TITLE PAGE:

In the References Cited, line 16, the Birken, S. et al. reference reads "Endoerinology", it should read --Endocrinology--.

In the Abstract on line 8, "delectable" should read --detectable--.

In claim 1, column 7, line 23 and in claim 19, column 8, lines 41 and 45, a chemical group which reads "carboxyl," each occurrence, should read --carboxy--.

In claim 2, column 7, line 39, "a" should read --an--.

In claim 11, column 8, line 7, "pr" should read --or--.

In claim 19, column 8, line 41, where it reads "essentially to," should read --essentially purified, serum-derived antibody directed specifically to--.

Signed and Sealed this

Tenth Day of March, 1992

Attest:

HARRY F. MANBECK, JR.

Attesting Officer

Commissioner of Patents and Trademarks